United States Patent
Fazlin et al.

(10) Patent No.: US 11,337,611 B2
(45) Date of Patent: May 24, 2022

(54) SYSTEMS AND METHODS FOR DETECTING INFECTIOUS PATHOGENS

(71) Applicant: Kaligia Biosciences, LLC, Largo, FL (US)

(72) Inventors: Fazal A Fazlin, St. Petersburg, FL (US); Arsenii Zhdanov, Clearwater, FL (US); Keith Michael Bunch, Holiday, FL (US)

(73) Assignee: KALIGIA BIOSCIENCES, LLC, Largo, FL (US)

( * ) Notice: Subject to any disclaimer, the term of this patent is extended or adjusted under 35 U.S.C. 154(b) by 0 days.

(21) Appl. No.: 17/195,739

(22) Filed: Mar. 9, 2021

(65) Prior Publication Data

US 2021/0307614 A1 Oct. 7, 2021

Related U.S. Application Data

(60) Provisional application No. 63/003,646, filed on Apr. 1, 2020.

(51) Int. Cl.
| | |
|---|---|
| *A61B 5/00* | (2006.01) |
| *G16H 50/80* | (2018.01) |
| *G16H 50/30* | (2018.01) |
| *A61B 10/00* | (2006.01) |

(52) U.S. Cl.
CPC .......... *A61B 5/0075* (2013.01); *A61B 5/7264* (2013.01); *G16H 50/30* (2018.01); *G16H 50/80* (2018.01); *A61B 10/0051* (2013.01)

(58) Field of Classification Search
None
See application file for complete search history.

(56) References Cited

U.S. PATENT DOCUMENTS

| | | | | |
|---|---|---|---|---|
| 5,463,223 A | * | 10/1995 | Wong | G01N 21/3563 250/339.07 |
| 2011/0212002 A1 | * | 9/2011 | Curry | B01L 3/50825 422/430 |
| 2013/0189641 A1 | * | 7/2013 | Perfect | A61B 1/24 433/29 |
| 2018/0348136 A1 | * | 12/2018 | Treado | G01J 3/44 |

(Continued)

OTHER PUBLICATIONS

Carlomagno et al, "COVID-19 salivary Raman fingerprint: innovative approach for the detection of current and past SARS-CoV-2 infections", Mar. 2, 2021, entire document. (Year: 2021).*

(Continued)

*Primary Examiner* — Michael W Kahelin
*Assistant Examiner* — Elizabeth K So
(74) *Attorney, Agent, or Firm* — Lewellyn Law, PLLC; Stephen Lewellyn

(57) ABSTRACT

Methods and systems are provided for detecting infectious pathogens in a saliva sample by using a Raman spectrometer to obtain Raman spectrum data of the saliva sample. A score is determined based on the Raman spectrum data using a machine learning, the score indicates whether an infectious pathogen is present in the saliva sample. In certain aspects, the methods and systems operate to determine if an individual is infected with COVID-19 based on Raman spectrum data of a saliva sample of the individual.

9 Claims, 8 Drawing Sheets

(56) References Cited

U.S. PATENT DOCUMENTS

2020/0337594 A1* 10/2020 Reddy .................. G01N 33/497
2021/0123883 A1*  4/2021 Tabib-Azar ...... G01N 33/56983

OTHER PUBLICATIONS

Barauna et al, "Ultra-rapid on-site detection of SARS-CoV-2 infection using simple ATR-FTIR spectroscopy and analysis algorithm: high sensitivity and specificity", Nov. 4, 2020, entire document. (Year: 2020).*

* cited by examiner

SYSTEMS AND METHODS FOR DETECTING INFECTIOUS PATHOGENS

CROSS-REFERENCE TO RELATED APPLICATIONS

This application claims the benefit of U.S. Provisional Patent Application Ser. No. 63/003,646, filed Apr. 1, 2020, the entirety of which is incorporated herein by reference.

FIELD OF THE INVENTION

The present disclosure relates to methods for detecting the presence of infectious pathogens in human saliva using Raman spectroscopy. In particular, this disclosure relates to detecting the presence of COVID-19 in human saliva using Raman spectroscopy.

BACKGROUND OF THE INVENTION

Infectious pathogens, whether bacterial, viral, or other origin, present acute and chronic challenges to human health. Many common infections affect the respiratory tract. Respiratory tract diseases, particularly infectious respiratory diseases of viral and bacterial origin, are prevalent in patients of all ages, although often are more serious in the very young and the very old. Viruses include DNA viruses and RNA viruses. Bacteria include Gram positive and Gram negative bacteria and may include *mycoplasma* (bacteria lacking cell walls). In addition to disease-causing bacteria, some diseases, such as, e.g., respiratory diseases, may be caused by other microorganisms such as yeasts, fungi, and other small, disease-causing organisms.

An example of a common viral cause of respiratory (and other) disorders in patients is the influenza ("flu") virus. Influenza ("flu") refers to disease caused by one of several related RNA viruses of the Orthomyxoviridae family, typified by fever, headache, fatigue, and other symptoms. There are different types of influenza; influenza A and influenza B are both about equally prevalent in humans. Identification of the strain of flu in a sample can help suggest treatments, can help suggest preventive measures to be taken, and can help to track such infections in a population.

Another example of a viral cause of respiratory disorder includes coronaviruses. Coronaviruses are a large family of viruses that usually cause mild to moderate upper-respiratory tract illnesses, like the common cold, in people[1]. There are hundreds of coronaviruses that affect animal species. Seven coronaviruses are known to cause human disease. Four of these coronaviruses are mild: viruses 229E, OC43, NL63 and HKU1; three of the coronaviruses can have more serious outcomes in people: SARS (severe acute respiratory syndrome), which emerged in late 2002 and disappeared by 2004; MERS (Middle East respiratory syndrome), which emerged in 2012 and remains in circulation in camels; and COVID-19, which emerged in December 2019 from China (a global effort is under way to contain its spread). COVID-19 is caused by the coronavirus known as SARS-CoV-2 (also known as 2019-nCoV).

Examples of common bacterial causes of respiratory (and other) disorders in patients include whooping cough, pneumonia, and tuberculosis. Whooping cough is caused by *Bordetella pertussis* and is typified by fits of violent coughing, which may persist for weeks. Pneumonia is the name given to respiratory disorders characterized by fluid in the lungs, coughing, fever, vomiting, fatigue, and other symptoms. Pneumonia may be caused by bacterial or viral infection; determination of the cause of a particular case is critical in determining the course of treatment of the patient. Causes of pneumonia include *Streptococcus pneumonia, Staphylococcus aureus*, adenovirus, influenza viruses, respiratory syncytial virus, *Pneumocystis, jirovecii* (a fungus), and other agents. Tuberculosis is caused by *Mycobacterium tuberculosis*, is typified by cough including spitting up blood, chest pain, chills, fever, night sweats, and other symptoms, and may be fatal.

Agents that cause infectious respiratory diseases typically differ between upper respiratory tract diseases and lower respiratory tract disorders; thus, the variety or range of bacterial or viral agents found in patients suffering from upper respiratory disorders may be different than those bacterial or viral agents found in patients suffering from lower respiratory disorders. However, successful diagnosis and treatment of respiratory diseases often requires identification of disease-causing organisms present in a clinical sample obtained from a subject suffering, or suspected of suffering, from an infectious respiratory disorder. Differentiating between organisms typical of upper respiratory and those typical of lower respiratory disorders may also be critical in the successful diagnosis and treatment of respiratory diseases. In addition, identification of other symptoms and sequelae of respiratory disorders may aid the successful diagnosis and treatment of respiratory diseases.

Some diseases may be detected by blood tests (e.g., dengue virus, Epstein-Barr virus, trypanosomal diseases, *plasmodium* diseases, and others). Some diseases may be detected by analysis of swabs or body fluids such as saliva, sweat and semen. Diseases may also be detected by analysis of urine or stool samples.

To be effective in treating such infectious disorders, rapid testing is essential. However, present methods and systems for testing are often time-consuming, inconvenient for patients, may require sample collection methods or amounts that are painful or uncomfortable for patients, and may be expensive. Methods that require large amounts of sample, or that require incubation of a sample for hours or days, are often ineffective at timely detection or identification of the cause of a respiratory disorder. This leads to drastic reduction in test effectiveness and adversely affects the spread of virus among the population.

Thus, improved methods, systems, and assays for the detection and identification of agents that cause diseases, such as influenza, respiratory diseases, viral diseases, bacterial diseases, and other diseases, are desired.

SUMMARY OF THE INVENTION

The present invention is directed to methods for detecting the presence of infectious pathogens in human saliva using Raman spectroscopy. In some aspects, the invention is directed to detecting the presence of COVID-19 in human saliva. In further aspects, the invention is directed to detecting the presence of COVID-19 using Raman spectroscopy. In one embodiment, the Raman spectral data holds information on the molecular composition of saliva. In one embodiment, individuals provide saliva for COVID-19 detection according to the methods of the invention. In a further embodiment, the same individuals are also tested for COVID-19 using laboratory tests. In another embodiment, the Raman spectral data and the laboratory test data from such individuals, both non-infected and infected with COVID-19, will be supplied to machine learning algorithms to predict the presence of COVID-19 in saliva.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

For a better understanding of the invention, its operating advantages and the specific objects attained by its uses, reference should be had to the accompanying drawings and descriptive matter in which there are illustrated embodiments of the invention.

BRIEF DESCRIPTION OF THE DRAWINGS

The following drawings illustrate by way of example and are included to provide further understanding of the invention for the purpose of illustrative discussion of the embodiments of the invention. No attempt is made to show structural details of the embodiments in more detail than is necessary for a fundamental understanding of the invention, the description taken with the drawings making apparent to those skilled in the art how the several forms of the invention may be embodied in practice. Identical reference numerals do not necessarily indicate an identical structure. Rather, the same reference numeral may be used to indicate a similar feature of a feature with similar functionality. In the drawings.

DETAILED DESCRIPTION OF THE INVENTION

Figure 1:
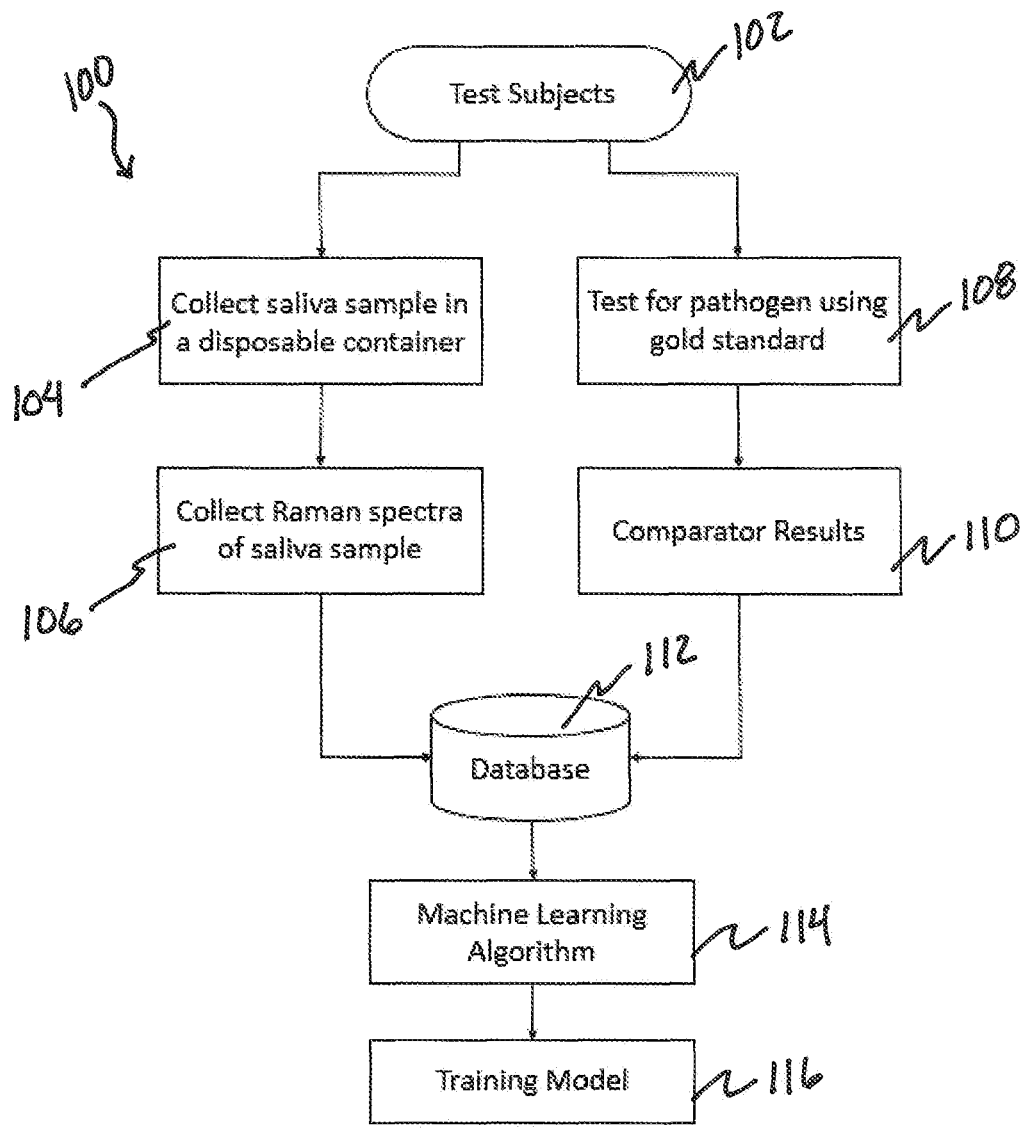
FIG. 1 shows a flowchart of an example method of saliva sample collection and machine learning training in accordance with embodiments of the invention.

Systems, methods, and devices for detecting the presence of one or more infectious agents in a single clinical sample, or in a plurality of aliquots of a single clinical sample, are provided.

In some embodiments, the invention is directed to systems, methods, and devices for testing for presence of one or more infectious pathogens in a single small-volume clinical sample, or aliquots thereof. In embodiments, the analysis of the small-volume clinical sample is completed in a short period of time. In embodiments, the infectious pathogens cause respiratory disease. In embodiments, the infectious pathogens cause a respiratory disease selected from an upper respiratory disease and a lower respiratory disease.

In some embodiments, the infectious disease is a bacterial disease, or a viral disease, or another type of disease, and analysis of the small-volume clinical sample determines whether the infectious pathogen is a bacterial disease, a viral disease, or another type of disease. The determination of the type of infectious pathogen aids in determining the type of treatment to provide to the subject, e.g., where the determination indicates the infectious pathogen is a fungal disease, the subject should be treated with anti-fungal drugs; where the determination indicates the infectious pathogen is a yeast infection, the subject should be treated with anti-yeast drugs; and so forth.

In some embodiments, the infectious disease is a bacterial disease. In embodiments, the analysis of the small-volume clinical sample determines whether the infectious disease is a bacterial disease.

In embodiments where the analysis of the small-volume clinical sample determines that the infectious disease is a bacterial disease, said determination indicates the use of antibiotics in the treatment of that disease. In other embodiments, the infectious disease is a viral disease.

In embodiments, the analysis of the small-volume clinical sample determines whether the infectious disease is a viral disease. In embodiments where the analysis of the small-volume clinical sample determines that the infectious disease is a viral disease, said determination indicates the use of antiviral drugs in the treatment of that disease.

In embodiments where the analysis of the small-volume clinical sample determines that the infectious disease is a viral disease, said determination indicates that antibiotics should not be used in the treatment of that disease. In embodiments, the infectious disease is a bacterial disease, or a viral disease. In embodiments, the analysis of the small-volume clinical sample determines whether the infectious disease is a bacterial disease or a viral disease. Similarly, where the analysis of the small volume clinical sample determines the infectious disease is a fungal disease, the subject should be treated with anti-fungal drugs; where the determination indicates the infectious disease is a yeast infection, the subject should be treated with anti-yeast drugs; and so forth.

In embodiments, the infectious disease comprises a respiratory disease. In embodiments, the infectious disease comprises a respiratory disease selected from an upper respiratory disease and a lower respiratory disease. In embodiments, the analysis of the small-volume clinical sample determines whether the infectious disease is an upper respiratory disease or a lower respiratory disease. In embodiments, the analysis of the small-volume clinical sample determines the type of upper respiratory disease or a lower respiratory disease present in the small volume clinical sample.

For example, in embodiments, the upper or lower respiratory disease is a bacterial disease, or a viral disease, or another type of disease, and the analysis of the small-volume clinical sample determines whether the upper or lower respiratory disease is a bacterial disease, a viral disease, or another type of disease. In embodiments where the analysis of the small-volume clinical sample determines that the upper or lower respiratory disease is a bacterial disease, said determination indicates the use of antibiotics in the treatment of that disease.

In embodiments where the analysis of the small-volume clinical sample determines that the upper or lower respiratory disease is a viral disease, said determination indicates the use of antiviral drugs in the treatment of that disease. In embodiments where the analysis of the small-volume clinical sample determines that the upper or lower respiratory disease is a viral disease, said determination indicates that antibiotics should not be used in the treatment of that disease. Similarly, where the analysis of the small volume clinical sample determines the upper or lower respiratory disease is a fungal disease, the subject should be treated with anti-fungal drugs; where the determination indicates the infectious disease is a yeast infection, the subject should be treated with anti-yeast drugs; and so forth.

In embodiments, the systems, methods and devices are configured for detecting one or more of the following infectious pathogens: adenovirus B, adenovirus C, adenovirus E, *Bordetella parapertussis, Bordetella pertussis, Mycobacterium tuberculosis* (MTB), *Staphylococcus aureus*, Methicillin-Resistant *Staphylococcus aureus* (MRSA), Group A *streptococcus*, and Group B *streptococcus, Moraxella* catarrhais, *Enterobacter aerogenes, Haemophilus parainfluenzae*, Metapneumo Virus, *Streptococcus pneumonia*, Parainfluenza Virus 1, Parainfluenza Virus 2, Parainfluenza Virus 3, SARS, Coronavirus OC43, Coronavirus NL63, Coronavirus MERS, Coronavirus HKU1, Coronavirus 229E, COVID-19, Klibsiella pneumonia phoE, *Klebsiella pneumonia* KPC, Bocavirus type 2,4, and Bocavirus type 1,3.

In embodiments, the systems, methods, and devices are configured for detecting one or more infectious pathogens, and in such systems, methods, and devices configured for detecting one or more infectious pathogens, the infectious pathogen is an influenza virus. In embodiments, such systems, methods, and devices are configured for detecting influenza A and/or influenza B. In embodiments, individuals provide saliva for detecting one or more infectious pathogens.

In a further embodiment, the same individuals are also tested for infectious pathogens using laboratory tests. Non-limiting laboratory tests detect one or more of the group of markers consisting of influenza Matrix Protein markers, influenza neuraminidase protein markers, influenza hemagglutinin markers, or other influenza markers. In embodiments, the analysis of the small-volume clinical sample determines whether the infectious disease is influenza. In embodiments, the analysis of the small-volume clinical sample determines the type of influenza present in the small volume clinical sample. In embodiments where the analysis of the small-volume clinical sample determines that the infectious pathogen is influenza (which is a viral disease), said determination indicates that antibiotics should not be used in the treatment of that disease. In embodiments where the analysis of the small-volume clinical sample determines that the infectious pathogen is influenza, said determination indicates that antiviral drugs should be used in the treatment of that disease.

In embodiments, the systems, methods, and devices are configured for detecting one or more coronavirus. In embodiments, non-limiting laboratory tests detect one or more coronavirus markers that are indicative of viruses: SARS, Coronavirus OC43, Coronavirus NL63, Coronavirus MERS, Coronavirus HKU1, Coronavirus 229E, COVID-19 (also known as SARS-CoV-2 and 2019-nCoV). In some embodiments, the analysis of the small-volume clinical sample determines whether the infectious pathogen is a coronavirus.

In particular embodiments, the analysis of the small-volume clinical sample determines whether the infectious pathogen is COVID-19. In embodiments, the analysis of the small-volume clinical sample determines the type of coronavirus present in the small volume clinical sample. In embodiments where the analysis of the small-volume clinical sample determines that the infectious pathogen is a coronavirus (which is a viral disease), said determination indicates that antibiotics should not be used in the treatment of that disease. In embodiments where the analysis of the small-volume clinical sample determines that the infectious pathogen is a coronavirus, said determination indicates that antiviral drugs should be used in the treatment of that disease.

Samples from the throat of a subject may be obtained, e.g., by a throat swab or providing saliva; samples obtained from the nose of a subject may be obtained, e.g., by a nasal swab. In embodiments, samples obtained from the throat and from the nose of a subject may be tested together. In embodiments, laboratory testing of samples obtained from the throat, or from the nose, or from both the nose and from the throat, may be tested by nucleic acid analysis; or by amino acid analysis (e.g., ELISA or other antibody-based or binding protein-based analysis); or by general chemistry analysis; or by cytometric analysis; or by combinations thereof.

For example, samples may be tested by nucleic acid analysis and by amino acid analysis. Such tests may be used to determine how long a subject has had an infection, for example, by noting the delay in rise of levels of antibodies indicative of a particular disease in the sample; or by tracking the rise in the levels of antibodies indicative of a particular disease in the sample over time (e.g., by repeated testing over time). Similarly, such testing may be used to detect, or to determine, the effect of treatment, by noting the delay in rise of levels of antibodies indicative of a particular disease in the sample; or by tracking the rise in the levels of antibodies indicative of a particular disease in the sample over time (e.g., by repeated testing over time).

In embodiments, samples from throat and from nose may be included in a single solution, and tested together. In embodiments, samples from throat and from nose may be in separate vessels (e.g., sample containers), but both included in a single cartridge, and the separate vessels tested at the same time. Such testing at the same time may comprise testing the vessels separately, or may include mixing the contents of the vessels and testing the mixture. In embodiments, the systems, methods, and devices may be configured to test for, or to detect a plurality of nucleic acid markers, protein markers, and cytometric markers, each marker being indicative of at least one or more diseases or conditions. In embodiments, the systems, methods, and devices may be configured to test for, or to detect a plurality of nucleic acid markers, protein markers, cytometric markers, cytokines, and markers of inflammation, each marker or cytokine being indicative of at least one disease or condition. In embodiments, the samples obtained from the subject are also studied by Raman spectroscopy.

In embodiments, the systems, methods, and devices are configured for identifying, or estimating, or otherwise determining the stage of an infection in a subject by detecting, or determining the amounts of, or both, both nucleic acid markers indicative of a particular infection and antibody markers indicative of the same infection. Such systems, methods, and devices may be used to detect, measure, and track such markers over time, effective to provide an estimate or determination of how recently an infection occurred. Such systems, methods, and devices may be used to detect, measure, and track such markers over time, effective to aid in evaluating the present status of a subject suffering from an infection.

Such systems, methods, and devices may be used to detect, measure, and track such markers over time, effective to aid in determining the likely prognosis of a subject suffering from an infection. For example, where nucleic acid markers indicative of a particular infection are relatively numerous, while antibody or other protein markers indicative of that particular infection are relatively sparse, then it can be estimated or determined that the infection is a recent infection; however, where nucleic acid markers indicative of a particular infection are relatively numerous, and antibody or other protein markers indicative of that particular infection are also relatively numerous, then it can be estimated or determined that the infection is not a recent infection, since the subject has had the time to produce infection-specific antibodies. Where nucleic acid markers indicative of a particular infection are relatively sparse, and antibody or other protein markers indicative of that particular infection are also relatively numerous, then it can be estimated or determined that the infection in a late stage, and indicates that the infection is waning, since such observations indicate that the subject is overcoming the infection.

In embodiments, the analysis of the small-volume clinical sample may be completed in a short period of time. Test results may be obtained within three hours, or two hours, or one hour, or ½ hour, or less from the time a sample is placed in a testing device for analysis. A sample may be placed in a testing device for analysis within five hours, or four hours, or three hours, or two hours, or one hour, or ½ hour, or less from the time a sample was obtained from a subject. Test results may be obtained within eight hours, seven hours, or six hours, or five hours, or three hours, or two hours, or one hour, or ½ hour, or less from the time a sample was obtained from a subject. In embodiments, the method may be performed in less than about 40 minutes.

In embodiments, the systems, methods, and devices are configured for detecting one or more disease-causing agents in a single clinical sample, or in a plurality of aliquots of a single clinical sample. In embodiments, a single clinical sample has a volume of less than about 1 mL, less than about 500 µL, or less than about 250 µL, or less than 150 µL, or less than about 100 µL, or less than about 50 µL, or less than about 25 µL, or less than about 10 µL, or less than about 5 µL, or less than about 1 µL, or less.

In embodiments, major components of the system of the invention include: a Raman spectrometer; a disposable sample container; a Calibration Cap; a Light Shield Cap, and Data Acquisition Software.

In some embodiments, an operator fills the sterile disposable container with a subject's saliva using a pipette and issues the specimen an identification number. The operator then launches the spectra acquisition software on a computer and enters a patient identification number into the system while the software performs self-check using the Calibration Cap. The operator installs the disposable sample container into the spectrometer and covers the sample container with the Light Shield Cap to prevent ambient light interference. The operator then uses the acquisition software to collect saliva Raman spectra. The collected data is then saved and uploaded to a database where it can be investigated. After the test, the operator disposes the disposable sample container. The subjects are additionally tested for an infectious pathogen, such as COVID-19, using standard procedures.

The positive/negative results are added to the database with corresponding specimen identification numbers. Machine learning algorithms are used to find patterns in saliva spectra, unique to the infectious pathogen (e.g., COVID-19). After collecting enough samples to create a reliable model, saliva spectra is used to perform rapid diagnosis (e.g., COVID-19 diagnosis).

It is to be understood that the use of specific machine learning algorithms or techniques (i.e., decision tree learning) is offered by way of example only and is not meant to be restrictive of the present disclosure. In other implementations, one or more alternative machine learning algorithms or techniques can also be used. Machine learning algorithms or techniques can include, but are not necessarily limited to classification, clustering, neural networks and so forth, and any combination thereof.

In FIG. 1, there is shown a flowchart of an example method 100 of sample collection and machine learning training. At Step 102, the method begins by starting the process of performing randomized clinical trials in a controlled environment to obtained diverse saliva samples with varied composition. The purpose of the process is to reduce bias in the training models and to help in detecting different strains of COVID-19.

At Step 104, collection of saliva samples in clinical settings are performed for analysis. In embodiments, the saliva samples are collected with disposable equipment to help eliminate contamination. For example, samples can be collected in a polystyrene cuvette with use of a disposable funnel. The cuvette can then be sealed using a rubber stopper, for example.

Figure 2:
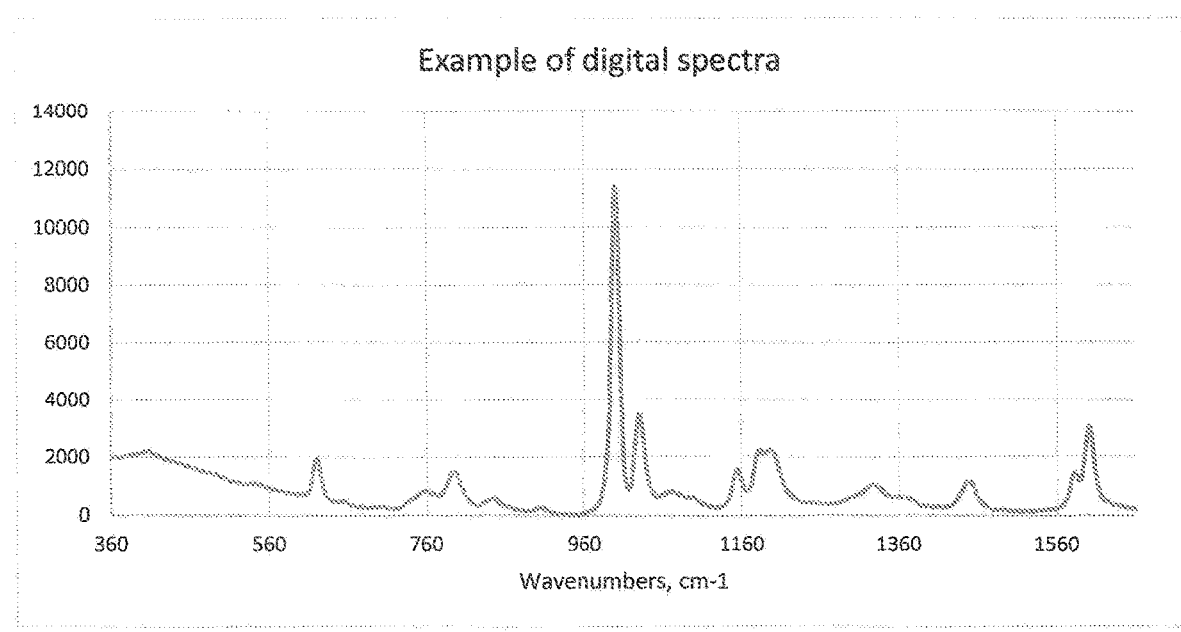
FIG. 2 is an example Raman spectrum of a saliva sample in accordance with embodiments of the invention.

At Step 106, the cuvette with the saliva sample is processed by a spectrometer, such as a Raman spectrometer. In embodiments, the cuvette inserted into a disposable opaque light shield cap with lock on clamps to hold the cuvette securely in place. The light shield cap is placed flush with an opaque sample holder. This is done to eliminate external light interference during collection of light spectrum readings. A CCD (Charge-Coupled Device) detector records the ambient light before the laser of the spectrometer is turned on. When the laser is turned on and incident on the saliva sample, a spectrum is produced which is recorded by CCD and saved as readings for that sample. An example Raman spectrum 200 that is produced is shown in FIG. 2. The readings are saved in database 108 for further comparison and machine learning in accordance with embodiments. Other vital readings that may affect the training of the machine learning algorithm are included in the database 112.

At Step 108, the individual from with the saliva sample is taken in Step 104 is concurrently tested to determine whether the individual is positive or negative for COVID-19. The concurrent tests can be any number of tests, such as, for example LDT—CDC modified protocol on easyMag+RotorGenes, Simplexa® COVID-19 Direct Kit—DiaSorin Molecular, NeuMoDx SARS-CoV-2 Assay—NeuMoDx, Xpert® Xpress SARS-CoV-2—Cepheid, and Abbott Alinity M SARS-CoV-2 PCR. The test results 110 data are also stored in database 108 for comparison with the spectrum reading produced in Step 104.

At Step 114, machine learning is used to process the data obtained in Steps 106 and 110 and stored in database 112. The data in database 112 are run through several machine learning algorithms to understand patterns in the spectral data between a COVID-19 positive sample and a COVID-19 negative sample.

From Step 114, a training model 116 can be developed with best sensitivity and specificity. A model can be described as a function, when provided with test data of a sample, will determine whether a sample is COVID-19 positive or negative.

While the foregoing description of method 100 is made in connection with specificity to detecting COVID-19 is an individual's saliva, it is envisioned that the foregoing method could be used to develop machine learning training models to detect other infections pathogens in saliva samples.

Figure 3:
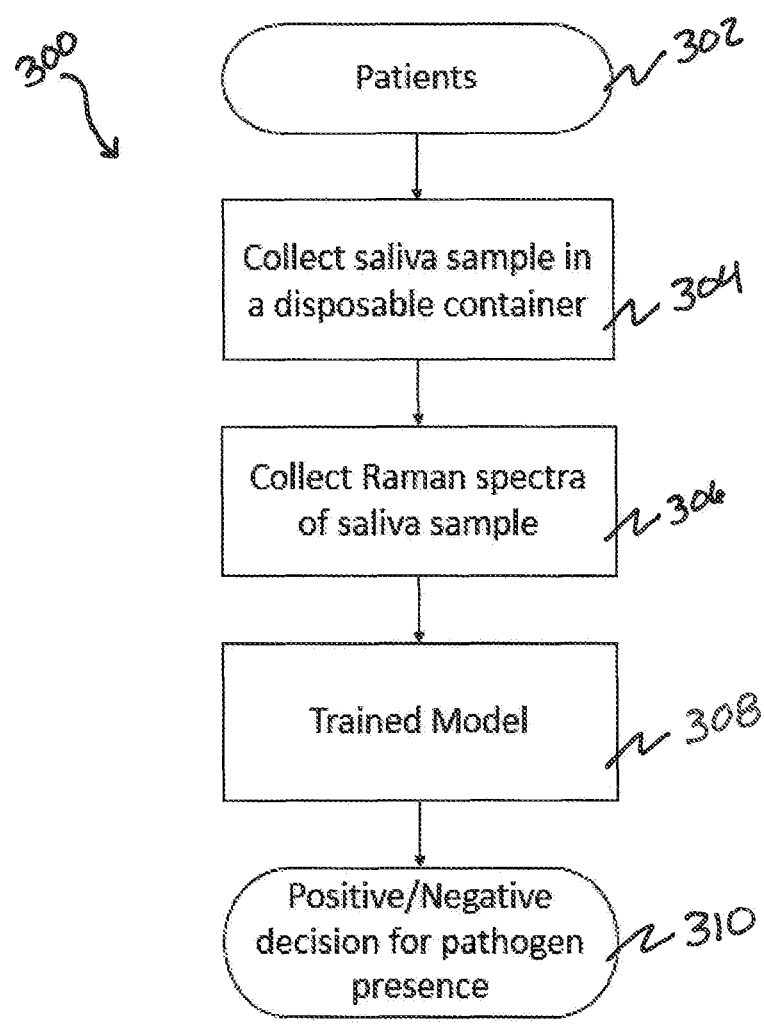
FIG. 3 shows a flowchart of an example method of saliva sample collection and testing of patients for an infectious pathogen in the saliva sample.

In FIG. 3, there is shown a flowchart of an example method 300 of sample collection and testing of patients for COVID-19. At Step 302, the method 300 begins with a patient presenting for testing. Then, at Step 304 a saliva sample is collected from the patient. In embodiments, the saliva sample can be collected using disposable equipment to help eliminate contamination. Further, in embodiments, the sample can be collected in a polystyrene cuvette with use of a disposable funnel. The cuvette can then be sealed using a rubber stopper.

At Step 306, the cuvette with the saliva sample is processed by a spectrometer, such as a Raman spectrometer. In embodiments, the cuvette with saliva sample is inserted into a disposable opaque light shield cap with lock on clamps to hold the cuvette securely in place. The light shield cap is placed flush with an opaque sample holder. This is done to eliminate external light interference during collection of light spectrum readings. A CCD (Charge-Coupled Device) detector records the ambient light before the laser is turned on. When the laser is turned on and incident on the saliva sample, a spectrum is produced which is recorded by CCD and saved as readings for that sample.

Then the collected readings for the sample are processed through the trained model 116 that was created in Step 114 of method 100. The model 116 is generated from training the machine learning algorithm with previous occurrences of saliva samples and their results. The scores generated by the model is used to categorize a sample as negative or positive for COVID-19, which the results are displayed at Step 310.

While the foregoing description of method 300 is made in connection with specificity to detecting COVID-19 is an individual's saliva, it is envisioned that the foregoing method could be used to detect other infections pathogens in saliva samples using machine learning models developed in accordance with embodiments of the invention.

Figure 4:
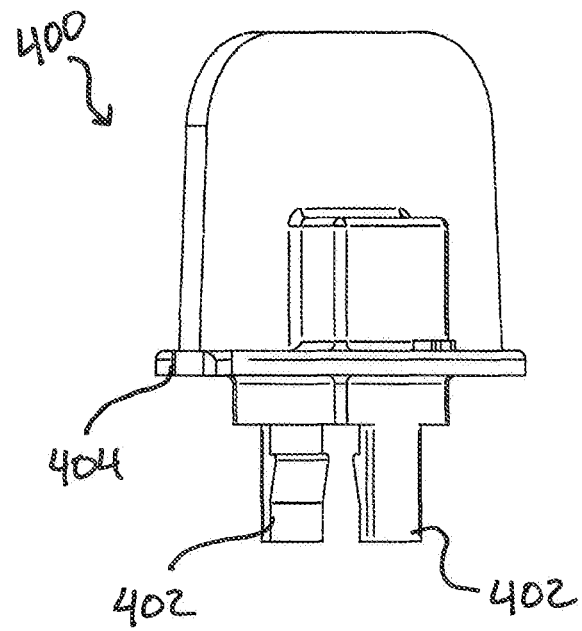
FIG. 4 is a diagrammatic view of a light shield cap in accordance with embodiments of the invention.

In FIG. 4, there is shown a light shield cap 400 in accordance with embodiments of the invention. The light shield cap 400 is designed to hold a sample container and prevent external light from interfering with the sample during scanning by a spectrometer. The light shield cap 400 is made of an opaque material to prevent external light from interfering with the sample during the scan. The light shield cap has lock-on clamps 402 that fit into a sample container lock-on grooves and hold it enclosed, as discussed in further detail below. The light shield cap also has ambient light enclosure lock-on tabs 404 (only one is shown the other is on the opposite side) that fit into an ambient light enclosure to ensure proper orientation of the sample container with the spectrometer lens, as further discussed below.

Figure 5:
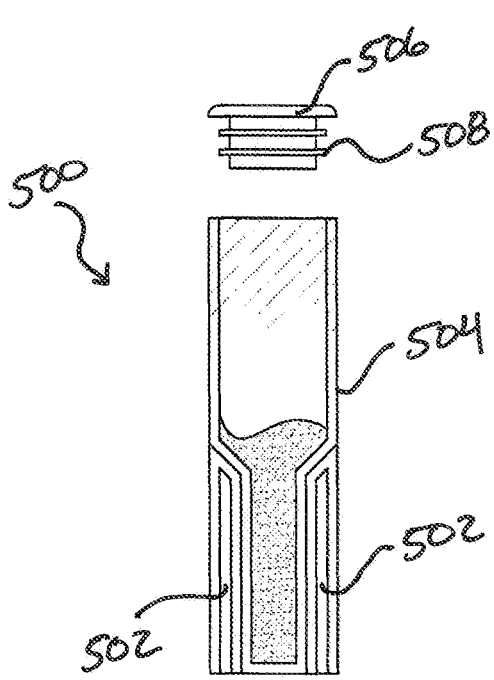
FIG. 5 is a diagrammatic view of a sample collection container in accordance with embodiments of the invention.

In FIG. 5 there is shown a sample container 500. In embodiments, the sample container 500 is made of transparent polystyrene to allow the laser beam of a spectrometer to pass through the container with minimum losses. The sample container 500 has lock-on grooves 502 on the sides 504 that fit the lock-on clamps 402 of the light shield cap 400 and hold the sample container enclosed in the light shield cap. In embodiments, a cap 506 is used to seal the open top of the sample container 500. In embodiments, the cap 506 has spill-proof grooves 508 to prevent the sample from spilling during handling.

Figure 6:
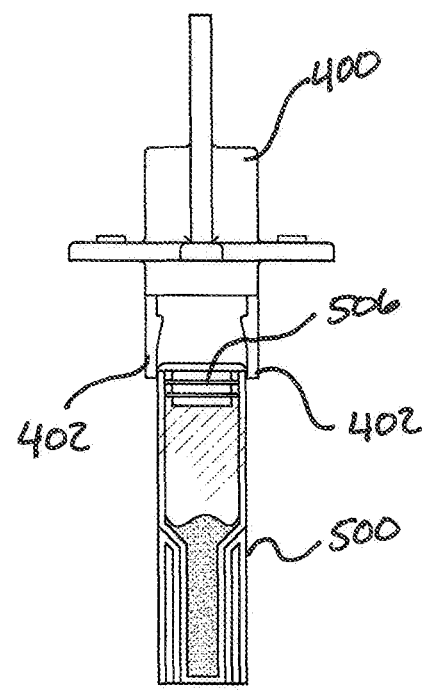
FIG. 6 is a diagrammatic view of a light shield cap partially secured to a sample container in accordance with embodiments of the invention.

In FIG. 6, there is shown the light shield cap 400 partially secured to the sample container 500. When fully secured, the top of the sample container 500 is inserted into the light shield cap 400 such that the upper portion of the sample container is shielded by the light shield cap and the lock-on clamps 402 are received by the lock-on grooves 502. For example, a capped sample container 500 is inserted into the light shield cap 400. The lock-on clamps 402 of the light shield cap 400 slide over the sample container surface. When the sample container 500 is fully inserted, the lock-on clamps 402 of the light shield cap 400 snap into the lock-on grooves 502 on the sample container 500 to firmly hold the sample container within the light shield cap.

Figure 7:
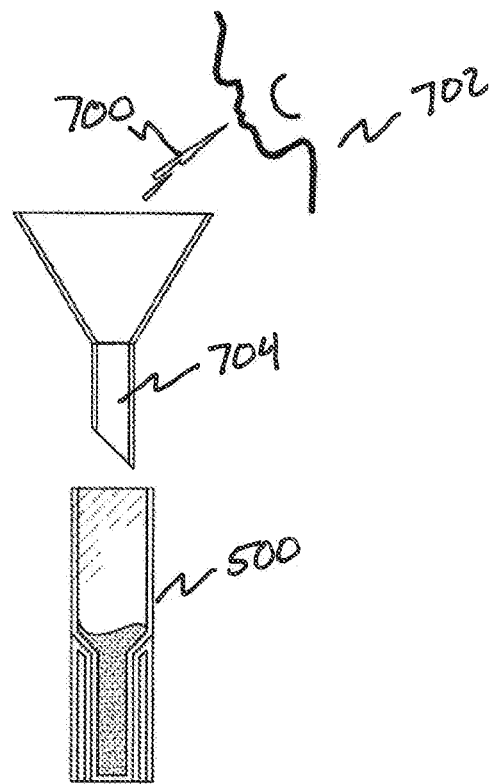
FIG. 7 is a diagrammatic view of a saliva sample being deposited in a sample container by an individual using a disposable funnel in accordance with embodiments of the invention.

In FIG. 7, there is shown a saliva sample 700 being deposited in the sample container 500 by an individual 702 using a disposable funnel 704. The lock-on grooves 502 can also be used as an indicating mark that shows that the container 500 is filled with enough sample. After collecting the sample, the sample container is closed with a container cap 506 (not shown here).

Figure 8:
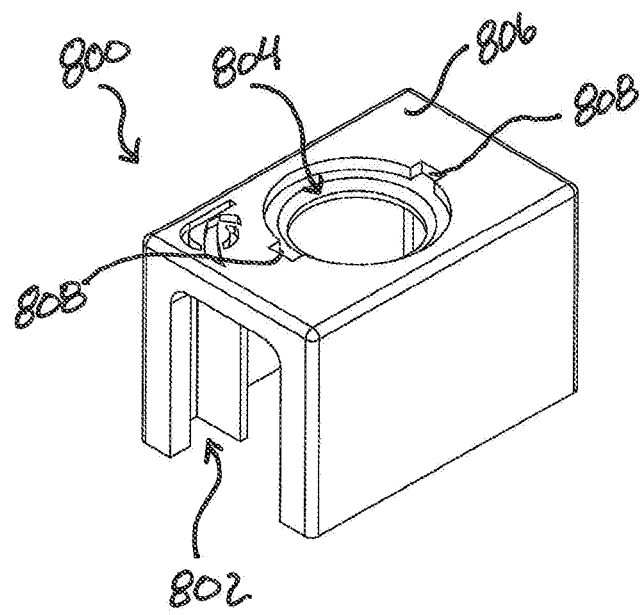
FIG. 8 is a diagrammatic view of an ambient light enclosure in accordance with embodiments of the invention.

In FIG. 8 there is shown an ambient light enclosure 800 in accordance with embodiments of the invention. The ambient light enclosure 800 is designed to cover the spectrometer lens of spectrometer, receive and retain the light shield cap 400, align the sample container 500 with the spectrometer, and prevent external light from interfering with the sample during the scan. The ambient light enclosure 800 is made of an opaque material to prevent external light from interfering with the sample during the scan.

The ambient light enclosure 800 has a groove 802 for receiving a spectrometer focusing ring with a firm connection to prevent external light from interfering with the sample during the scan and ensures the consistent focal distance between the spectrometer lens and the sample container. An opening 804 on the top 806 of the ambient light enclosure 800 has light shield cap notches 808 that that fit the ambient light cap lock-on tabs to prevent external light from interfering with the sample during the scan and ensure proper orientation of the sample container. The relation between opening 804 and the groove 802 for proper alignment with the spectrometer lens to ensure the consistent focal distance between the spectrometer lens and the sample container.

Figure 9:
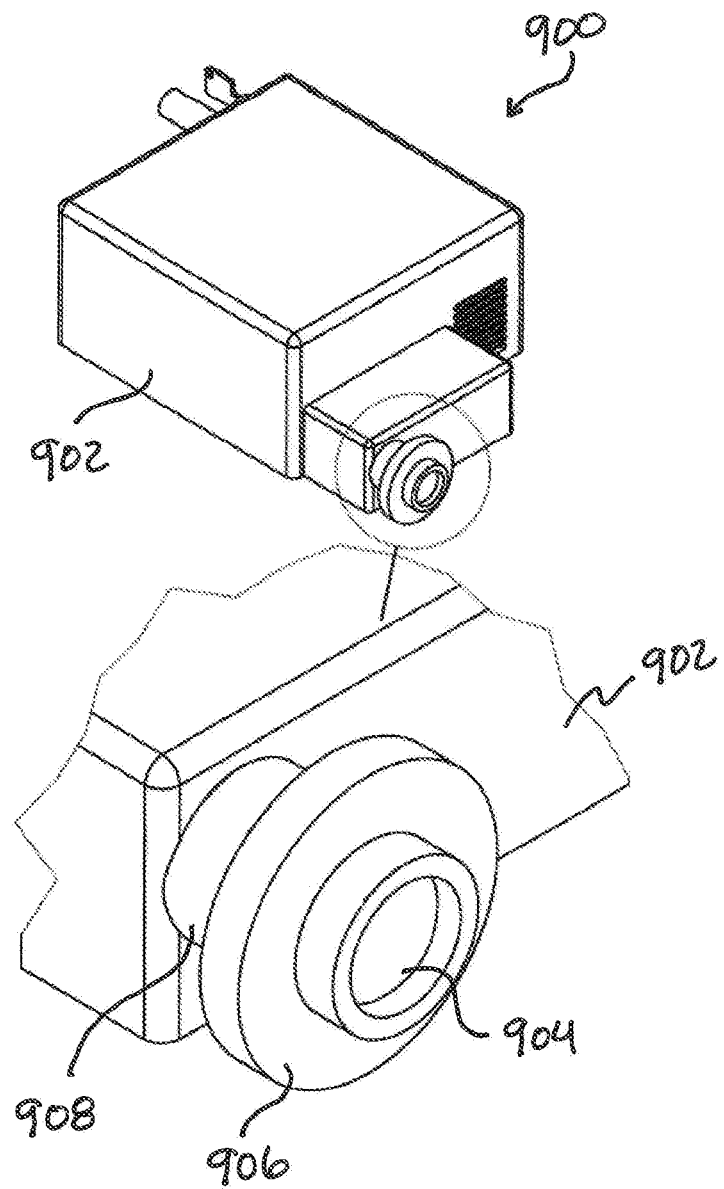
FIG. 9 is a diagrammatic view of a spectrometer in accordance with embodiments of the invention.

In FIG. 9 there is diagrammatically shown a spectrometer 900 in accordance with embodiments of the invention. The embodiments, the spectrometer 900 consists of a main optics enclosure 902 that houses the laser, CCD camera, diffraction gratings, control boards and other optical and electrical components required to acquire the Raman spectra. The spectrometer laser output is coupled through a lens system that consists of a spectrometer lens 904, a spectrometer focusing ring 906, and spectrometer threaded tube 908. The spectrometer lens 904 is installed in the spectrometer threaded tube 908. The spectrometer focusing ring 906 is attached to the spectrometer threaded tube 908 and secured to ensure a consistent focal distance between the spectrometer lens and the sample Container.

Figure 10:
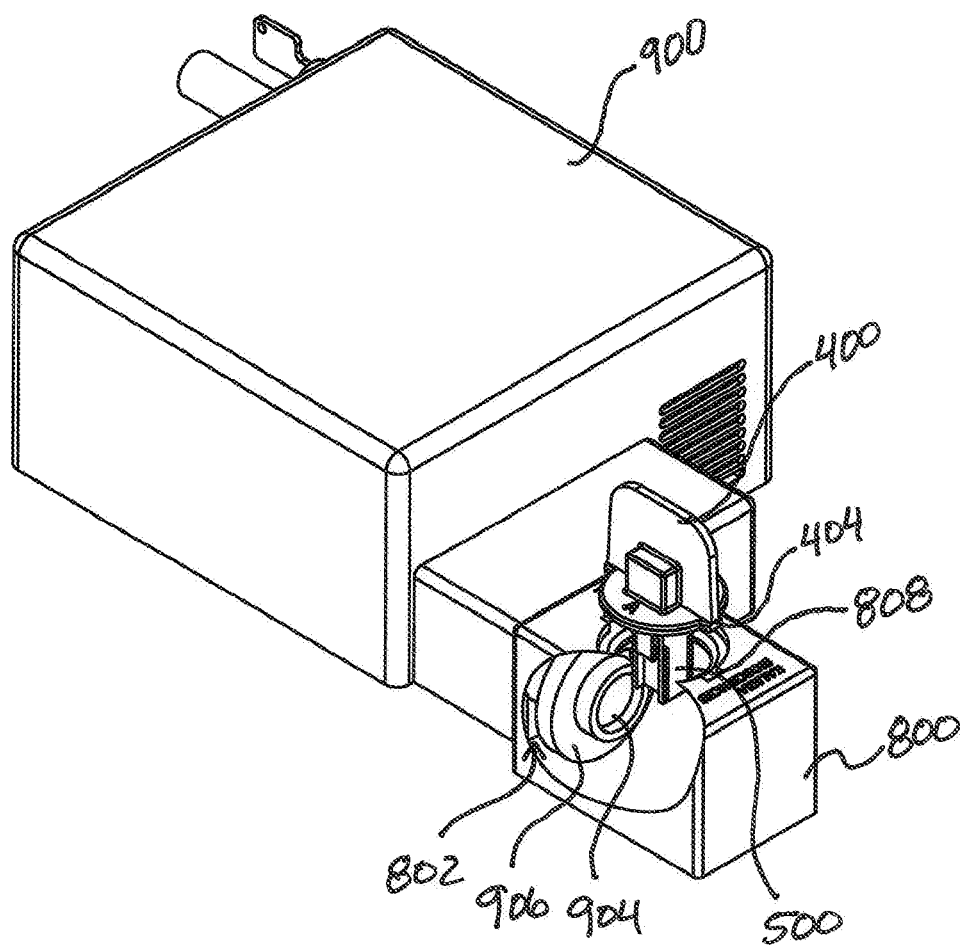
FIG. 10 diagrammatically shows a spectrometer and a sample contained by a sample container being inserted into an ambient light enclosure for analysis by the spectrometer in accordance with embodiments of the invention.

In FIG. 10 there is diagrammatically shown the spectrometer 900 and a sample contained by container 500 being inserted into the ambient light enclosure 800 for analysis. As shown, the ambient light enclosure 800 is secured to the spectrometer 900 with the spectrometer focusing ring 906 disposed within the groove 802 of the light enclosure, which ensures a consistent focal distance between the spectrometer lens 904 and the sample container 500. The light shield cap 400 is shown attached to and holding the sample container. The light shield cap 400, with the attached sample container 500, is being inserted into the opening 804 in the ambient light enclosure 800. The light shield cap lock-on tabs 404 are aligned with the ambient light shield notches 808 to ensure proper orientation of the sample container 500 with the spectrometer lens 904. Raman Spectrum of the sample is then collected by the spectrometer 900 and subjected to the machine learning algorithms to produce a score indicating either presence or absence of the pathogen in the sample.

After the light Shield cap 400 and the ambient light enclosure 800 have been connected to the spectrometer 900, the operator can initiate the test initiates. When the test is initiated, the spectrometer activates the laser. The laser light is focused on the sample inside the sample container using the spectrometer lens. When laser light interacts with the sample, it generates Raman signal. Raman signal scatters on the sample, the part of the Raman signal that scatters in the direction of the Spectrometer is focused on a narrow slit or grating inside the spectrometer using the spectrometer Lens. The narrow slit or grating uses diffraction to decompose the Raman signal. The decomposed Raman signal then strikes the Charge-coupled device (CCD).

The CCD is composed of a single or multiple arrays of individual pixels. Each pixel is a light sensitive element that produces electrical current based on the intensity of incident light, where pixel position in the CCD corresponds to the wavelength of the decomposed Raman signal. When the portion of the decomposed Raman signal hits the pixel, it produces electrical current. Electrical current from each individual pixel is then subjected to discretization using an analog-to-digital converter. After processing current form every pixel, the analog-to-digital converter generates a digital data array (digital spectrum) that carries information of the Sample molecular structure. The digital spectrum represents the Raman spectrum and is saved in the database.

During the sample collection, the spectrometer may also collect other data, including but not limited to data collection time, dark noise, and multiple scans of the same sample.

The following describes an example method of machine learning and sample testing in accordance with embodiments of the invention. To determine whether the acquired saliva spectrum carries COVID-19 positive signatures or not, machine learning algorithms are used. Samples, may be confirmed by a PCR comparator method, to compose the training data set to create Automated Training Models (ATRs).

In an example, a dataset for machine learning contained a total of 6263 samples. The date was cleaned of outliers using validation flags and transformed using signal processing. Data was split into portions to create ATRs. Leave-one-out cross validation was used to evaluate model performance. Results were derived following the flowchart shown in FIG. 11, which shows a machine learning and sample analysis method according to embodiments of the invention.

Figure 11:
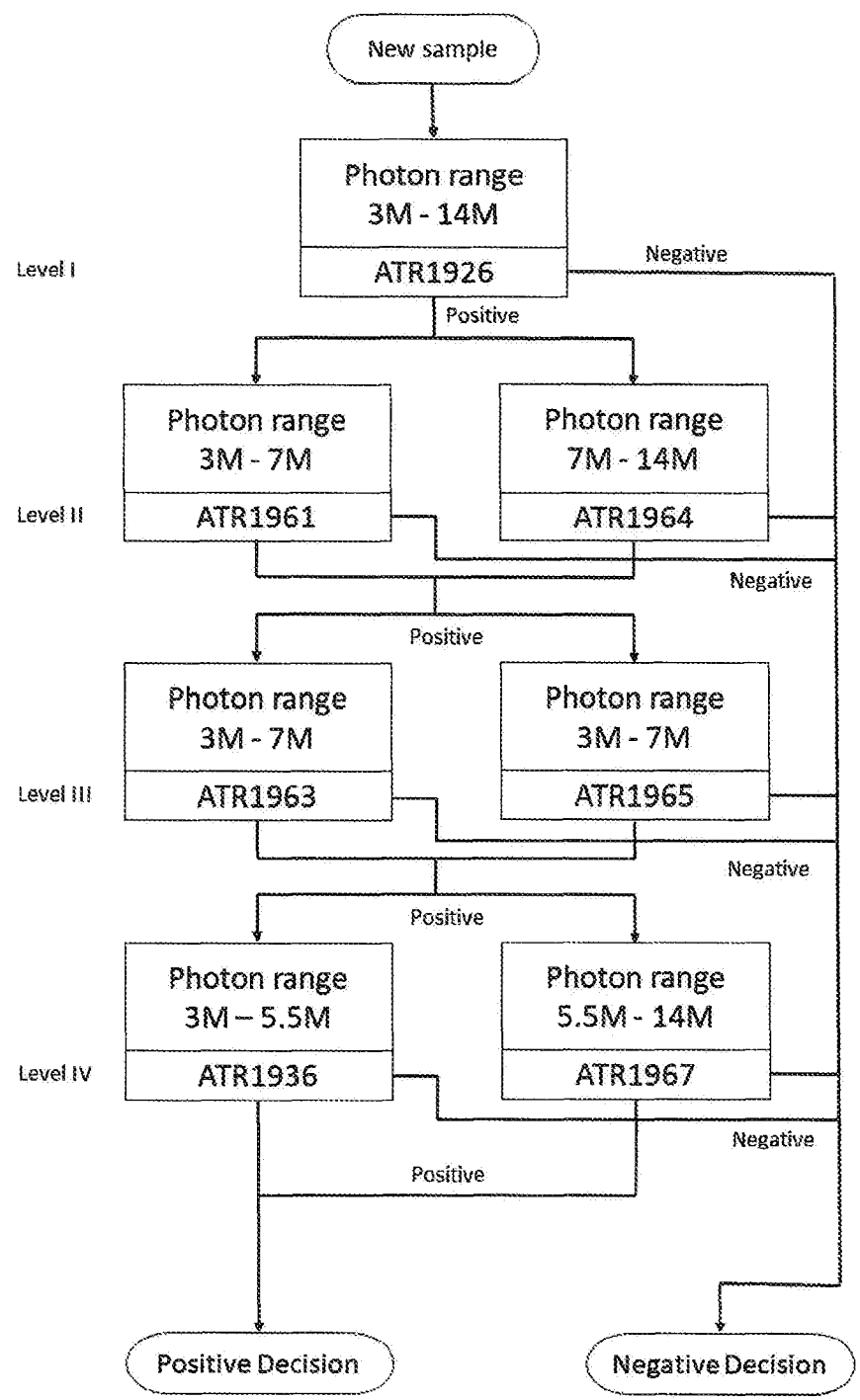
FIG. 11 shows a flowchart of an example machine learning training method and sample testing method in accordance with embodiments of the invention.

With reference to FIG. 11, after digital spectrum is collected, the total sum of pixel values (total photon count) is calculated to determine which steps of machine learning algorithm, this spectrum will be subjected to. During Level I, all spectra with total photon count in range 3e6 to 14e6 are subjected to ATR1926. Spectra with total photon count outside this range are discarded as invalid and do not produce a result. If ATR1926 produces a negative result, the system decides that the Sample is negative for the COVID-19 infection. If ATR1926 produces a positive result, the spectrum is the suggested to testing in Level II. In Level II, the test ATR is chosen based on the total photon count of the spectrum. If the spectrum is in the 3e6 to 7e6 range, it is being subjected to ATR1961, if it is in the 7e6 to 14e6 range, it is being subjected to ATR1964. If the selected model produces a negative result, the system decides that the Sample is negative for COVID-19 infection. If the selected model produces a positive result, the spectrum is then subjected to testing in Level III and Level IV. If at any level, the prediction is negative, the system decides that the Sample is negative for COVID-19 infection. If in all the levels, the prediction is positive, the system decides that the Sample is positive for COVID-19 infection.

Table 1 below compliments the flowchart of FIG. 11 and shows what algorithms, and their parameters are used at each level of testing. In each level, starting from the top, the system selects what ATR to use based on the incoming spectra total photon count. Each ATR was built using the arrays of spectra with comparator methods (described below), classification algorithm 1 or 2 and a parameter threshold. Parameter threshold is a cutoff value. After an ATR produces a score, if it is below the threshold, the decision is negative. If the ATR score is above the threshold, the decision is positive. On every level, if the decision is negative, the system decides that the Sample is negative for COVID-19 infection. If on every level, the decision is positive, system decides that the Sample is positive for COVID-19 infection.

TABLE 1

Machine learning algorithms level parameters.

| Level | ATR | Photon Range (in millions) | Classification Algorithm | Algorithm Threshold |
|---|---|---|---|---|
| I | 1926 | 3-14 | 2 | 0.5 |
| II | 1961 | 3-7 | 2 | 0.5 |
|  | 1964 | 7-14 | 2 | 0.5 |
| III | 1963 | 3-7 | 1 | 0.5 |
|  | 1965 | 7-14 | 2 | 0.5 |
| IV | 1936 | 3-5.5 | 2 | 0.75 |
|  | 1967 | 5.5-14 | 2 | 0.75 |

Algorithm Description.

Classification Algorithm 1 uses the Mahalanobis Distance for this method, PCA (Principal Component Analysis) computes the covariance and regularization is used to reduce bias if it is present.

Classification Algorithm 2 Uses Logistic Regression

The training model is fitted by using Python's sklearn-linear_model.LogisticRegression classifier function and the transformed training data. Logistic regression is a linear classifier that models the conditional probability of the label(s) Y and variable X; P(Y|X). Algorithm parameters are optimized to minimize the error between actual values and predicted values. The data is in a fixed random order so that the results are consistent each time the algorithm is run.

The algorithm implements regularized logistic regression by using the LibLinear library. LibLinear is a Library for Large Linear Classification. L2 regularization is used to avoid overfitting by penalizing high-valued regression coefficients. The L2 penalty is equal to the square of the magnitude of coefficients.

The inverse of regularization strength $(1/\lambda)$ is 500. This value determines the strength of regularization thereby regulating against overfitting. As $1/\lambda$ decreases, the strength of regularization increases.

A One-vs-Rest (OvR) strategy is used to fit the binary labels by training a single classifier per class where the samples of that class are positive, and all other samples are negatives. The base classifiers produce a real-valued confidence score to make the decision.

The iteration stopping criteria is 1e-4. While iterating and computing multicollinearity, the tolerance signals the algorithm to stop iterating once the delta between one value and the next is less than 1e-4. The maximum iterations for this algorithm to converge is 1000.

Other algorithm parameters such as fit_intercept, intercept_scaling, and class_weight are kept at the default values. Regression coefficients, estimated on training data by using the Logistic Regression algorithm and saved in the models, and utilized to get binary predictions for the new test data.

Classification Algorithm Discrimination Threshold.

The decision for predicting probability into a class is controlled by a parameter referred to as the discrimination threshold. While optimizing algorithm parameters, the default value for this threshold was 0.5. Threshold was adjusted to optimize Sensitivity and Specificity metrics.

Automated Training Model Input Datasets.

ATR 1926. To build this model, digital spectra paired with the comparator method results, were subjected to Machine Learning Classification Algorithm 2. Algorithm details descried above. Data to create the model was collected during clinical trials and is summarized below in Table 2. Leave-one-out cross validation was used to evaluate model performance.

TABLE 2

Machine Learning Classification Algorithm 2 Data.

| Type | Dimension | P | N | Sum |
| --- | --- | --- | --- | --- |
| Total | Total | 658 | 3545 | 4203 |
| Spectrometer | KBS-0011 | 87 | 413 | 500 |
| Spectrometer | KBS-0017 | 99 | 3 | 102 |
| Spectrometer | KBS-0018 | 77 | 601 | 678 |
| Spectrometer | KBS-0016 | 85 | 165 | 250 |
| Spectrometer | KBS-0015 | 0 | 637 | 637 |
| Spectrometer | KBS-0012 | 43 | 381 | 424 |
| Spectrometer | KBS-0014 | 82 | 574 | 656 |

TABLE 2-continued

Machine Learning Classification Algorithm 2 Data.

| Type | Dimension | P | N | Sum |
| --- | --- | --- | --- | --- |
| Spectrometer | KBS-0020 | 50 | 35 | 85 |
| Spectrometer | KBS-0019 | 68 | 31 | 99 |
| Spectrometer | KBS-0021 | 67 | 12 | 79 |
| Spectrometer | KBS-0022 | 0 | 428 | 428 |
| Spectrometer | KBS-0023 | 0 | 265 | 265 |
| Location | Kaligia Labs | 1 | 3545 | 3546 |
| Location | TGH | 657 | 0 | 657 |
| Cross-Validation | Sensitivity | 0.964 | Specificity | 0.995 |

ATR1961. To build this model, digital spectra paired with the comparator method results, were subjected to Machine Learning Classification Algorithm 2. Algorithm details descried above. Data to create the model was collected during clinical trials and is summarized below in table 3. Leave-one-out cross validation was used to evaluate model performance.

TABLE 3

ATR1961 Training Data.

| Type | Dimension | P | N | Sum |
| --- | --- | --- | --- | --- |
| Total | Total | 528 | 1680 | 2208 |
| Spectrometer | KBS-0011 | 75 | 240 | 315 |
| Spectrometer | KBS-0016 | 80 | 1 | 81 |
| Spectrometer | KBS-0017 | 83 | 5 | 88 |
| Spectrometer | KBS-0018 | 57 | 304 | 361 |
| Spectrometer | KBS-0015 | 0 | 444 | 444 |
| Spectrometer | KBS-0012 | 53 | 322 | 375 |
| Spectrometer | KBS-0014 | 6 | 0 | 6 |
| Spectrometer | KBS-0019 | 61 | 43 | 104 |
| Spectrometer | KBS-0020 | 56 | 44 | 100 |
| Spectrometer | KBS-0021 | 57 | 18 | 75 |
| Spectrometer | KBS-0022 | 0 | 140 | 140 |
| Spectrometer | KBS-0023 | 0 | 119 | 119 |
| Location | Kaligia Labs | 1 | 1675 | 1676 |
| Location | TGH | 527 | 5 | 532 |
| Cross-Validation | Sensitivity | 0.931 | Specificity | 0.985 |

ATR1964. To build this model, digital spectra paired with the comparator method results, were subjected to Machine Learning Classification Algorithm 2. Algorithm details descried above. Data to create the model was collected during clinical trials and is summarized below in table 4. Leave-one-out cross validation was used to evaluate model performance.

TABLE 4

ATR1964 Training Data.

| Type | Dimension | P | N | Sum |
| --- | --- | --- | --- | --- |
| Total | Total | 528 | 1680 | 2208 |
| Spectrometer | KBS-0011 | 75 | 240 | 315 |
| Spectrometer | KBS-0016 | 80 | 1 | 81 |
| Spectrometer | KBS-0017 | 83 | 5 | 88 |
| Spectrometer | KBS-0018 | 57 | 304 | 361 |
| Spectrometer | KBS-0015 | 0 | 444 | 444 |
| Spectrometer | KBS-0012 | 53 | 322 | 375 |
| Spectrometer | KBS-0014 | 6 | 0 | 6 |
| Spectrometer | KBS-0019 | 61 | 43 | 104 |
| Spectrometer | KBS-0020 | 56 | 44 | 100 |
| Spectrometer | KBS-0021 | 57 | 18 | 75 |

TABLE 4-continued

ATR1964 Training Data.

| Type | Dimension | P | N | Sum |
|---|---|---|---|---|
| Spectrometer | KBS-0022 | 0 | 140 | 140 |
| Spectrometer | KBS-0023 | 0 | 119 | 119 |
| Location | Kaligia Labs | 1 | 1675 | 1676 |
| Location | TGH | 527 | 5 | 532 |
| Cross-Validation | Sensitivity | 0.935 | Specificity | 0.983 |

ATR1963. To build this model, digital spectra paired with the comparator method results, were subjected to Machine Learning Classification Algorithm 1. Algorithm details descried above. Data to create the model was collected during clinical trials and is summarized below in Table 5. Leave-one-out cross validation was used to evaluate model performance.

TABLE 5

ATR1963 Training Data.

| Type | Dimension | P | N | Sum |
|---|---|---|---|---|
| Total | Total | 431 | 497 | 928 |
| Spectrometer | KBS-0011 | 52 | 0 | 52 |
| Spectrometer | KBS-0016 | 67 | 114 | 181 |
| Spectrometer | KBS-0017 | 88 | 72 | 160 |
| Spectrometer | KBS-0018 | 38 | 43 | 81 |
| Spectrometer | KBS-0014 | 12 | 15 | 27 |
| Spectrometer | KBS-0012 | 13 | 0 | 13 |
| Spectrometer | KBS-0019 | 58 | 49 | 107 |
| Spectrometer | KBS-0020 | 51 | 50 | 101 |
| Spectrometer | KBS-0021 | 52 | 55 | 107 |
| Spectrometer | KBS-0023 | 0 | 22 | 22 |
| Spectrometer | KBS-0015 | 0 | 36 | 36 |
| Spectrometer | KBS-0022 | 0 | 41 | 41 |
| Location | TGH | 427 | 213 | 640 |
| Location | AdventHealth Tampa | 4 | 112 | 116 |
| Location | Kaligia Labs | 0 | 172 | 172 |
| Cross-Validation | Sensitivity | 0.837 | Specificity | 0.586 |

ATR1965. To build this model, digital spectra paired with the comparator method results, were subjected to Machine Learning Classification Algorithm 2. Algorithm details descried above. Data to create the model was collected during clinical trials and is summarized below in Table 6. Leave-one-out cross validation was used to evaluate model performance.

TABLE 6

ATR1965 Training Data.

| Type | Dimension | P | N | Sum |
|---|---|---|---|---|
| Total | Total | 431 | 497 | 928 |
| Spectrometer | KBS-0011 | 52 | 0 | 52 |
| Spectrometer | KBS-0016 | 67 | 114 | 181 |
| Spectrometer | KBS-0017 | 88 | 72 | 160 |
| Spectrometer | KBS-0018 | 38 | 43 | 81 |
| Spectrometer | KBS-0014 | 12 | 15 | 27 |
| Spectrometer | KBS-0012 | 13 | 0 | 13 |
| Spectrometer | KBS-0019 | 58 | 49 | 107 |
| Spectrometer | KBS-0020 | 51 | 50 | 101 |
| Spectrometer | KBS-0021 | 52 | 55 | 107 |
| Spectrometer | KBS-0023 | 0 | 22 | 22 |

TABLE 6-continued

ATR1965 Training Data.

| Type | Dimension | P | N | Sum |
|---|---|---|---|---|
| Spectrometer | KBS-0015 | 0 | 36 | 36 |
| Spectrometer | KBS-0022 | 0 | 41 | 41 |
| Location | TGH | 427 | 213 | 640 |
| Location | AdventHealth Tampa | 4 | 112 | 116 |
| Location | Kaligia Labs | 0 | 172 | 172 |
| Cross-Validation | Sensitivity | 0.941 | Specificity | 0.986 |

ATR1936. To build this model, digital spectra paired with the comparator method results, were subjected to Machine Learning Classification Algorithm 2. Algorithm details descried above. Data to create the model was collected during clinical trials and is summarized below in Table 7. Leave-one-out cross validation was used to evaluate model performance.

TABLE 7

ATR1993 Training Data.

| Type | Dimension | P | N | Sum |
|---|---|---|---|---|
| Total | Total | 770 | 4659 | 5429 |
| Spectrometer | KBS-0011 | 99 | 531 | 630 |
| Spectrometer | KBS-0017 | 122 | 243 | 365 |
| Spectrometer | KBS-0018 | 86 | 678 | 764 |
| Spectrometer | KBS-0016 | 105 | 336 | 441 |
| Spectrometer | KBS-0015 | 0 | 637 | 637 |
| Spectrometer | KBS-0012 | 57 | 446 | 503 |
| Spectrometer | KBS-0014 | 87 | 662 | 749 |
| Spectrometer | KBS-0020 | 65 | 126 | 191 |
| Spectrometer | KBS-0019 | 76 | 184 | 260 |
| Spectrometer | KBS-0021 | 73 | 122 | 195 |
| Spectrometer | KBS-0022 | 0 | 428 | 428 |
| Spectrometer | KBS-0023 | 0 | 266 | 266 |
| Location | Kaligia Labs | 1 | 3546 | 3547 |
| Location | TGH | 762 | 1062 | 1824 |
| Location | AdventHealth Tampa | 7 | 51 | 58 |
| Cross-Validation | Sensitivity | 0.208 | Specificity | 0.952 |

ATR1967. To build this model, digital spectra paired with the comparator method results, were subjected to Machine Learning Classification Algorithm 2. Algorithm details descried above. Data to create the model was collected during clinical trials and is summarized below in Table 8. Leave-one-out cross validation was used to evaluate model performance.

TABLE 8

ATR1967 Training Data.

| Type | Dimension | P | N | Sum |
|---|---|---|---|---|
| Total | Total | 138 | 1841 | 1979 |
| Spectrometer | KBS-0011 | 15 | 225 | 240 |
| Spectrometer | KBS-0017 | 13 | 39 | 52 |
| Spectrometer | KBS-0016 | 12 | 112 | 124 |
| Spectrometer | KBS-0015 | 0 | 254 | 254 |
| Spectrometer | KBS-0012 | 13 | 178 | 191 |
| Spectrometer | KBS-0014 | 10 | 295 | 305 |
| Spectrometer | KBS-0018 | 8 | 267 | 275 |
| Spectrometer | KBS-0019 | 22 | 73 | 95 |
| Spectrometer | KBS-0020 | 20 | 51 | 71 |
| Spectrometer | KBS-0021 | 25 | 55 | 80 |
| Spectrometer | KBS-0022 | 0 | 167 | 167 |
| Spectrometer | KBS-0023 | 0 | 125 | 125 |
| Location | Kaligia Labs | 0 | 1574 | 1574 |
| Location | TGH | 136 | 256 | 392 |

TABLE 8-continued

ATR1967 Training Data.

| Type | Dimension | P | N | Sum |
|---|---|---|---|---|
| Location | AdventHealth Tampa | 2 | 11 | 13 |
| Cross-Validation | Sensitivity | 0.281 | Specificity | 0.964 |

Again, it is important to note that the foregoing specific machine learning and testing method and related data is an example in accordance with embodiments of the invention.

While the invention herein disclosed has been described by means of specific embodiments and applications thereof, numerous modifications and variations could be made thereto by those skilled in the art without departing from the scope of the invention set forth in the following claims.

What is claimed is:

1. A method for detecting the presence of COVID-19 in a saliva sample, the method comprising the steps of:
   providing a saliva sample in a sterile disposable container having a light shield cap attached to the disposable container;
   the sterile disposable container having lock-on grooves on sides thereof;
   the light shield cap having lock-on clamps that are engaged with the grooves and secure the light shield cap to the sterile disposable container with a top portion of the sterile disposable container being shielded from ambient light by the light shield cap;
   providing a spectrometer having an attached ambient light enclosure configured to shield ambient light from interfering with the operation of the spectrometer;
   engaging the sterile disposable container containing the saliva sample with the ambient light enclosure to align the disposable container with a lens of the spectrometer;
   performing Raman spectroscopy on the saliva sample to create Raman spectrum data of the saliva sample; and
   determining a score based on the Raman spectrum data, the score indicating whether COVID-19 is present in the saliva sample.

2. The method of claim 1, wherein the determining is performed by a machine learning algorithm trained to classify the Raman spectrum data for the presence of COVID-19.

3. The method of claim 1, wherein the ambient light enclosure has an opening on its top through which the sterile disposable container is inserted to be engaged with the ambient light enclosure, and the ambient light enclosure having notches that receive tabs on the light shield cap, the notches located to align the sterile disposable container with the lens of the spectrometer.

4. The method of claim 1, wherein the ambient light enclosure has a groove in which is disposed a focusing ring of the spectrometer.

5. The method of claim 3, wherein the opening and the groove are configured to provide a consistent focal distance between the spectrometer lens and the sterile disposable container.

6. The method of claim 1, wherein the top portion of the sterile disposable container is inserted into the light shield cap.

7. A method for detecting the presence of a coronavirus in a saliva sample, the method comprising the steps of:
   providing a saliva sample in a sterile disposable container having a light shield cap attached to the disposable container;
   the sterile disposable container having lock-on grooves on sides thereof;
   the light shield cap having lock-on clamps that are engaged with the grooves and secure the light shield cap to the sterile disposable container with a top portion of the sterile disposable container being shielded from ambient light by the light shield cap;
   providing a spectrometer having an attached ambient light enclosure configured to shield ambient light from interfering with the operation of the spectrometer;
   engaging the sterile disposable container containing the saliva sample with the ambient light enclosure to align the disposable container with a lens of the spectrometer;
   performing Raman spectroscopy on the saliva sample to create Raman spectrum data of the saliva sample;
   determining a score based on the Raman spectrum data, the score indicating whether a coronavirus is present in the saliva sample;
   wherein the infectious pathogen is COVID-19;
   wherein the ambient light enclosure has an opening on its top through which the sterile disposable container is inserted to be engaged with the ambient light enclosure, and the ambient light enclosure having notches that receive tabs on the light shield cap, the notches located to align the sterile disposable container with the lens of the spectrometer;
   wherein the ambient light enclosure has a groove in which is disposed a focusing ring of the spectrometer; and
   wherein the opening and the groove are configured to provide a consistent focal distance between the spectrometer lens and the sterile disposable container.

8. The method of claim 7, wherein the determining is performed by a machine learning algorithm trained to classify the Raman spectrum data for the presence of COVID-19.

9. The method of claim 7, wherein the top portion of the sterile disposable container is inserted into the light shield cap.

* * * * *